United States Patent [19]

Labroo

[11] Patent Number: 5,389,646
[45] Date of Patent: Feb. 14, 1995

[54] METHODS FOR TREATMENT AND PREVENTION OF BONE LOSS USING 2,3-BENZOPYRANS

[75] Inventor: Virender M. Labroo, Mill Creek, Wash.

[73] Assignee: ZymoGenetics, Inc., Seattle, Wash.

[21] Appl. No.: 175,899

[22] Filed: Dec. 30, 1993

[51] Int. Cl.$^6$ ............... A61K 31/445; A61K 31/40; A61K 31/35

[52] U.S. Cl. .................... 514/320; 514/422; 514/456; 514/457

[58] Field of Search ............ 514/456, 457, 412, 415, 514/291

[56] References Cited

U.S. PATENT DOCUMENTS

| | | | |
|---|---|---|---|
| 3,471,520 | 10/1969 | Irmscher et al. | 260/345.2 |
| 4,210,644 | 7/1980 | Ewing et al. | 424/239 |
| 4,489,056 | 12/1984 | Himmelstein et al. | 424/22 |
| 4,644,012 | 2/1987 | Tsuda et al. | 514/456 |
| 5,254,568 | 10/1993 | Kapil et al. | 514/320 |
| 5,280,040 | 1/1994 | Labroo et al. | 514/422 |

OTHER PUBLICATIONS

Broulik, *Endocrin. Reg.* 25: 217–219, 1991.
Saeed et al., *J. Med. Chem.* 33: 3210–3216, 1990.
Sharma et al., *J. Med. Chem.* 33: 3216–3222, 1990.
Sharma et al., *J. Med. Chem.* 33: 3222–3229, 1990.
Ray et al., *J. Med. Chem.* 19: 276–279, 1976.

*Primary Examiner*—Marianne M. Cintins
*Assistant Examiner*—T. J. Criares
*Attorney, Agent, or Firm*—Gary E. Parker

[57] ABSTRACT

Methods and pharmaceutical compositions for reducing bone loss are disclosed. 2,3-diaryl-1-benzopyrans and their pharmaceutically acceptable salts are formulated into medicaments for the treatment of bone loss due to osteoporosis or other conditions. Formulations include tablets and other forms suitable for oral administration and controlled-release subdermal implants.

21 Claims, 2 Drawing Sheets

METHODS FOR TREATMENT AND PREVENTION OF BONE LOSS USING 2,3-BENZOPYRANS

BACKGROUND OF THE INVENTION

Bone remodeling is the dynamic process whereby skeletal mass and architecture are renewed and maintained. This renewal and maintenance is a balance between bone resorption and bone formation, with the osteoclast and the osteoblast considered the two key participants in the remodeling process. The osteoclast initiates the remodeling cycle by resorbing a cavity in the bone which is subsequently refilled when the osteoblast synthesizes and deposits new bone matrix into the excavation. The activities of osteoclast and osteoblast are regulated by complex interactions between systemic hormones and the local production of growth factors and cytokines at active remodeling sites.

Imbalances in bone remodeling are associated with such conditions as osteoporosis, Paget's disease, and hyperparathyroidism. Osteoporosis, characterized by a decrease in the skeletal mass, is one of the most common diseases of postmenopausal women and is often the cause of debilitating and painful fractures of the spine, hip and wrist.

Approximately 25% of all postmenopausal women suffer from osteoporosis, and it is generally accepted that the etiology of the disease involves the reduction of circulating estrogens (Komm et al., *Science* 241:81–84, 1988). Komm et al. further report that the proportion of caucasian women in the United States who are at risk for a hip fracture is 15%, or 247 000 hip fractures per year in women over the age of 45.

The costs of osteoporosis, both personal and financial, are enormous. In 1984, 145,000 in-patient fracture reductions and 107,000 hip arthroplasties and replacements were performed on American women over 65 years of age. Among patients who lived alone prior to hip fracture, 15% to 20% required long-term care as a result of the fracture and one year after the fracture had still not regained their independence. The total financial cost of osteoporosis treatment, including fractures, in the United States in 1986 was 7–10 billion dollars (Peck et al., *Am. J. Med.* 84:275–282, 1988).

Bone loss associated with osteoporosis has been arrested by the administration of exogeneous estrogens. To be effective, estrogen therapy must begin within a few years of the onset of menopause, and should continue for 10 to 15 years, according to Thorneycroft (*Am. J. Obstet. Gynecol.* 160:1306–1310, 1989). While there are several different types of estrogens, 17-$\beta$-estradiol is the primary estrogen found naturally occurring in premenopausal women and is often the compound of choice for therapeutic use. At the recommended dose, however, there are significant side effects, the most disturbing being the well-established correlation of estrogen therapy with endometrial and breast cancers. The incidence of carcinoma is both dose-dependent and duration-dependent.

Avoidance of the cancer risk has been achieved by the concomitant use of a progestogen with estrogen. This combination, however, causes menses to return, which many women find unacceptable. A further disadvantage is that the long-term effects of the progestogen have not been fully determined. Thus, a large population of women require alternatives to hormone replacement therapies that can safely prevent the rapid bone loss that accompanies the menopause.

Certain substituted 2,3-diaryl-1-benzopyrans have been shown to have antiestrogenic activity with little or no estrogenicity, and have been proposed for use in the treatment of breast cancer. See Kapil et al., U.S. Pat. No. 5,254,568; Saeed et al., *J. Med. Chem.* 33: 3210–3216, 1990; Sharma et al., *J. Med. Chem.* 33: 3222–3229, 1990; and Sharma et al., *J. Med. Chem.* 33: 3216–3222, 1990. These compounds have not previously been shown to have an effect on bone resorption.

There remains a need in the art for compositions and methods useful in reducing bone loss, in particular bone loss associated with osteoporosis. There is a further need for such compositions that lack the undersirable side effects of estrogens. The present invention provides such compositions and methods and also provides other, related advantages.

DESCRIPTION OF THE INVENTION

Figure 1:
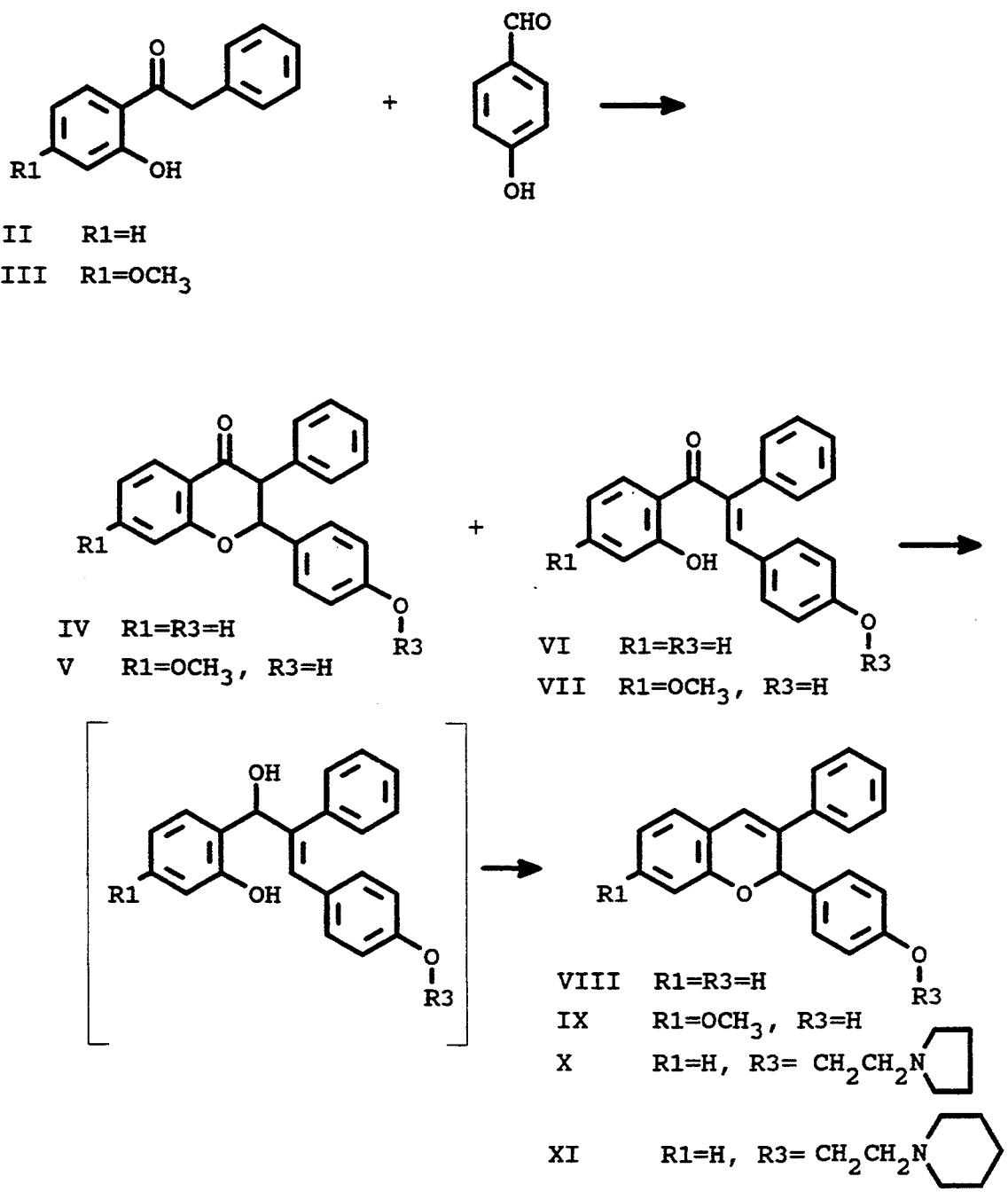
FIG. 1 illustrates the preparation of certain compounds useful within the present invention.

Within the present invention, 2,3-diaryl-1-benzopyrans and their salts are used within human and veterinary medicine for the regulation of bone metabolism. These compounds may be used, for example, in the treatment of patients suffering from or at risk for bone loss due to osteoporosis (including post-menopausal osteoporosis and glucocorticoid-related osteoporosis), Paget's disease, hyperparathyroidism, hypercalcemia of malignancy and other conditions characterized by excessive rates of bone resorption and/or decreased rates of bone formation.

The 2,3-diaryl-1-benzopyrans used within the present invention are defined by the general formula I:

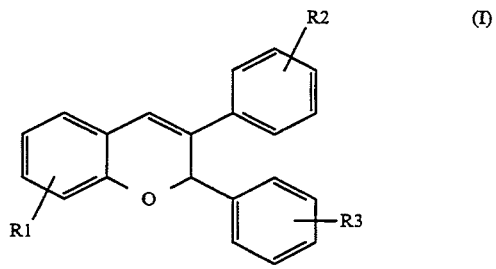

wherein each of R1 and R2 is individually H, OH, linear or branched chain $C_1$–$C_{17}$ alkoxy, linear or branched chain $C_2$–$C_{18}$ acyhloxy, or linear or branched chain $C_2$–$C_{18}$ alkoxycarbonyl; and R3 is

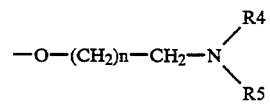

wherein each of R4 and R5 is individually a linear or branched chain alkyl radical of from one to 18 carbon atoms, or together with N, R4 and R5 form a three- to 10-membered ring; and n is an integer from 1 to 6, preferably 1–3, most preferably 1. Preferably, each of R4 and R5 is individually methyl, ethyl, propyl, isopropyl, butyl, isobutyl, sec-butyl or tert-butyl, or together with N, R4 and R5 form a five- or six-membered ring. Most preferably, R3 is

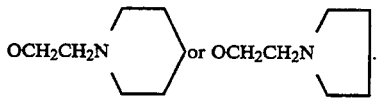

Within preferred embodiments, the compounds I have the structure:

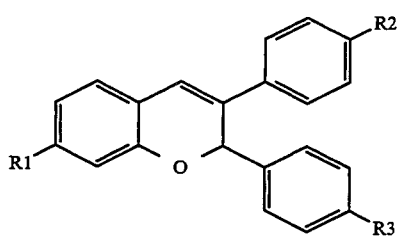

Within other preferred embodiments, R1 and R2 are alkoxy. Within other preferred embodiments, R1 and R2 are individually H, OH or $C_1$–$C_4$ alkoxy, $C_2$–$C_5$ alkoxycarbonyl or $C_2$–$C_5$ acyloxy. R3 is preferably a 2-piperidinoethoxy radical. Within other preferred embodiments, R1 and R2 are individually H or OH. As used herein, the term "acyloxy" refers to radicals of the structure

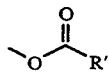

wherein R' is linear or branched chain alkyl or aminoalkyl.

Particularly preferred compounds for use within the present invention include:

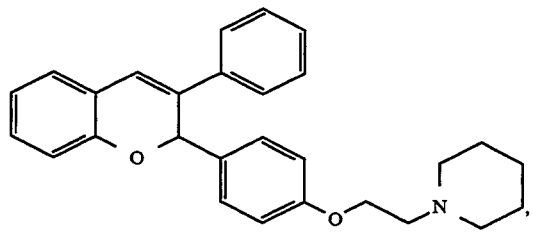

i.e. R1=R2=H and R3 is:

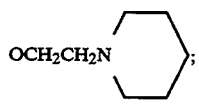

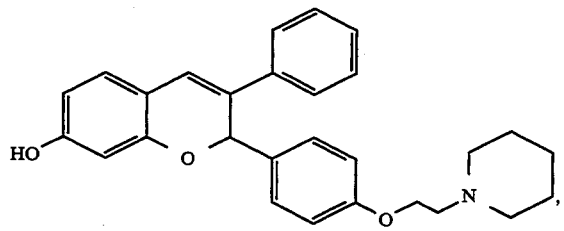

i.e. R1=OH, R2=H, and R3 is:

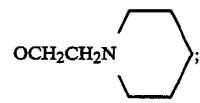

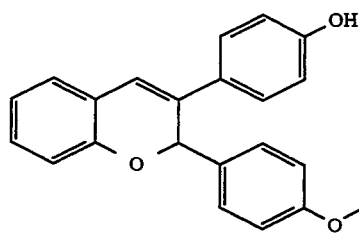

i.e. R1=H, R2=OH, and R3 is:

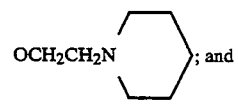

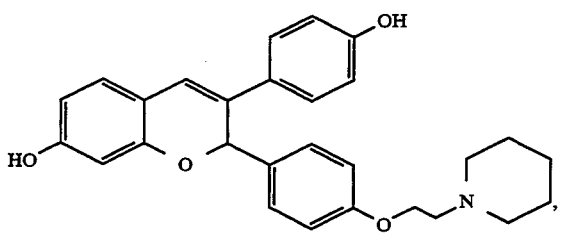

i.e. R1=R2=OH and R3 is:

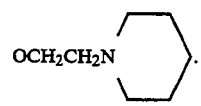

Although it is preferred to use the 2,3-diaryl-2H-1-benzopyrans disclosed above, 2,3-diaryl-1-benzopyrans substituted at the 2 position may also be used for reducing bone loss. Preferred substitutions in this regard include methyl, ethyl, propyl and butyl. In addition, each of the aromatic rings of I can be further substituted at one or more positions with a moiety such as OH; fluoro; $CF_3$; CN; a linear alkyl, alkoxy or acyloxy radical of from one to eighteen carbon atoms; a branched alkyl, alkoxy or acyloxy radical of from three to eighteen carbon atoms; $NO_2$; $NH_2$ or NHCOR", wherein R" is a linear or branched chain alkyl radical of from one to eighteen carbon atoms. Those skilled in the art will recognize that substitutions should generally be limited in number and/or size so as not to disrupt the function of the molecule due to large changes in solubility, receptor interactions, biological activity, etc. Thus, substitutions are preferably limited in number and will consist of groups of smaller size, e.g. lower ($C_1$-$C_4$) alkyl radicals.

Benzopyrans of the formula I can be prepared according to the methods disclosed in Saeed et al., *J. Med. Chem.* 33: 3210–3216, 1990; Sharma et al., *J. Med. Chem.* 33: 3222–3229, 1990; and U.S. Pat. No. 5,254,568, which are incorporated herein by reference in their entirety. A representative synthetic scheme is illustrated in FIG. 1. Base-catalyzed condensation of desoxybenzoin II with 4-hydroxybenzaldehyde yields a mixture of the dihydro-4H-1-benzopyran-4-one IV and the 2-phenylchalcone VI. Similarly, condensation of desoxybenzoin III with 4-hydroxybenzaldehyde gives a mixture of the dihydrobenzopyran-4-one V and the 2-phenylchalcone VII. Reduction of the phenylchalcones VI and VII with sodium borohydride followed by thermal cyclodehydration of the alcohols yields the 2H-benzopyran phenols VIII and IX, respectively. Compounds VIII and IX are then alkylated to produce the ethers X and XI, respectively. Hydroxy derivatives of I (i.e. those in which at least one of R1 and R2 is OH) can be prepared as disclosed by Sharma et al. (ibid.) and in U.S. Pat. No. 5,254,568 by condensation of appropriately OTHP (O-tetrahydropyranyl) protected hydroxy derivatives of desoxybenzoin with 4-hydroxybenzaldehyde. Phenolic derivatives having a piperidinoethoxy residue on 2-phenyl are prepared by starting from THP ethers of the appropriate desoxybenzoins, thereby allowing selectivity in attachment of the side chain to the requisite OH group.

Synthesis of 2,3-diaryl-1-benzopyrans substituted at one or more positions on the aromatic rings is carried out using conventional synthetic techniques from suitable precursors, e.g. substituted desoxybenzoins and/or substituted benzaldehydes, such as 4-hydroxy-3-methoxybenzaldehyde, 3,4-dihydroxybenzaldehyde, or 2,4-dihydroxybenzaldehyde.

Within the present invention, 2,3-diaryl-1-benzopyrans may be prepared in the form of pharmaceutically acceptable salts, especially acid-addition salts, including salts of organic acids and mineral acids. Examples of such salts include salts of organic acids such as formic acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulfuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

For use within the present invention, 2,3-diaryl-1-benzopyrans and their pharmaceutically acceptable salts are formulated with a pharmaceutically acceptable carrier to provide a medicament for parenteral, oral, nasal, rectal, subdermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release subdermal implants, tablets, etc. One skilled in the art may formulate the compounds in an appropriate manner, and in accordance with accepted practices, such as those disclosed in *Remington's Pharmaceutical Sciences,* Gennaro, ed., Mack Publishing Co., Easton, Pa., 1990 (which is incorporated herein by reference in its entirety.)

Oral administration is preferred. Thus, the active compound is prepared in a form suitable for oral administration, such as a tablet or capsule. Typically, a pharmaceutically acceptable salt of the compound is combined with a carrier and molded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, coloring, etc.

Pharmaceutical compositions are administered at daily to weekly intervals. An "effective amount" of such a pharmaceutical composition is the amount that provides a clinically significant inhibition of bone loss. Such amounts will depend, in part, on the particular condition to be treated, age, weight, and general health of the patient, and other factors evident to those skilled in the art. In general, inhibition of bone loss is manifested as a statistically significant difference in cancellous bone volume between treatment and control groups. This can be seen as, for example, a 5–10% or more difference in spinal bone mass or bone mineral content over two years. Data from accepted animal models, such as the ovariectomized mouse or rat models of osteoporosis, are generally predictive of doses in humans to within one order of magnitude. These animal models mimic the post-menopausal condition and are generally recognized models of osteoporosis. Therapeutic doses for the treatment of osteoporosis will generally range from 0.01–50 mg/kg/day, preferably 0.05–10 mg/kg/day, most preferably 0.1–5.0 mg/kg/day.

The pharmaceutical compositions may be administered in unit dosage form on a daily to weekly basis. In the alternative, they may be provided as controlled release formulations suitable for subdermal implantation. Implants are formulated to provide release of active compound over the desired period of time, which can be up to several years. Controlled-release formulations are disclosed by, for example, Sanders et al., *J. Pharm. Sci.* 73: 1294–1297, 1984; U.S. Pat. No. 4,489,056; and U.S. Pat. No. 4,210,644, which are incorporated herein by reference.

The following example is offered by way of illustration, not limitation.

EXAMPLE

2-[4-(2-piperidinoethoxy)phenyl]-3-phenyl-2H-1-benzopyran was obtained from the Central Drug Research Institute, Lucknow, India. The compound was designated CDRI 85/287. The effects of CDRI 85/287 on bone resorption were measured in ovariectomized rats. Two-month-old female Sprague Dawley rats weighing at least 200 grams were pre-labeled with 3H-tetracycline (Du Pont NEN Research Products, Boston, Mass.; 19.6 GBq/mmol, 0.53 Ci/mmol, radiochemical purity=98.6%) by intraperitoneal injection of 15 μCi of $^3$H-tetracycline 3 times per week. Three days after the final prelabel injection, the rats were randomized to the following treatment groups (10 animals per group):

a) sham/vehicle (placebo)
b) ovariectomized (OVX)/vehicle
c) OVX/CDRI 85/287; 15 mg pellet=1 mg/day/kg in 250 g rat d) OVX/17β-estradiol; 0.5 mg pellet=35 μg/day/kg in 250 g rat e) OVX/combination pellet (CDRI 85/287+estradiol)

f) baseline controls

CDRI 85/287 and 17β-estradiol (E$_2$) were implanted subcutaeously as sustained release pellets. Pellets containing a matrix of cholesterol, lactose, celluloses, phosphates and stearates were prepared by Innovative Research of America (Toledo, Ohio). The pellets were designed to release the hormone over a 60-day period.

Surgical procedures were performed with animals under general anesthesia (ketamine/xylazine). A small, midline, dorsal skin incision was made halfway between the middle of the back and base of the tail. Entrance into the peritoneal cavity was gained through two muscle incisions made one-half to two-thirds of the way down each side of the body. The ovary was pulled out through the muscle incision and severed with a single cut at the junction of the Fallopian tube and uterine horn. The uterine horn was returned to the peritoneal cavity, and one or two sutures were used to close the muscle layer. After both ovaries were removed, the pellet was implanted subcutaneously through the skin incision and placed in the area of the middle back. The skin was closed using skin clips to discourage chewing of the incision sites.

The rats were housed two per cage and maintained on a 12-hour light/dark schedule at approximately 70° F. They were pair fed with each pair receiving 40 g. of a balanced ration (Harlan/Teklad Laboratories #8604; obtained from Animal Specialities, Inc., Hubbard, Oreg.) per day and free choice water. Body weights were monitored regularly throughout the experiment. On days two and eight prior to sacrifice, the rats received an intraperitoneal injection of calcein green at 15 mg/kg as a fluorescent bone marker to be used in histomorphometric measurements of specific bone sections.

Animals were sacrificed on day 57 or 58 following surgery. Tibiae were removed and cleaned of remaining soft tissue. The proximal 1 cm section was dehydrated with a series of alcohols and chloroform to remove remaining fat and tissue. Bone density of this section was determined using the Archimedes principle (bone weight÷bone volume in water).

Figure 2:
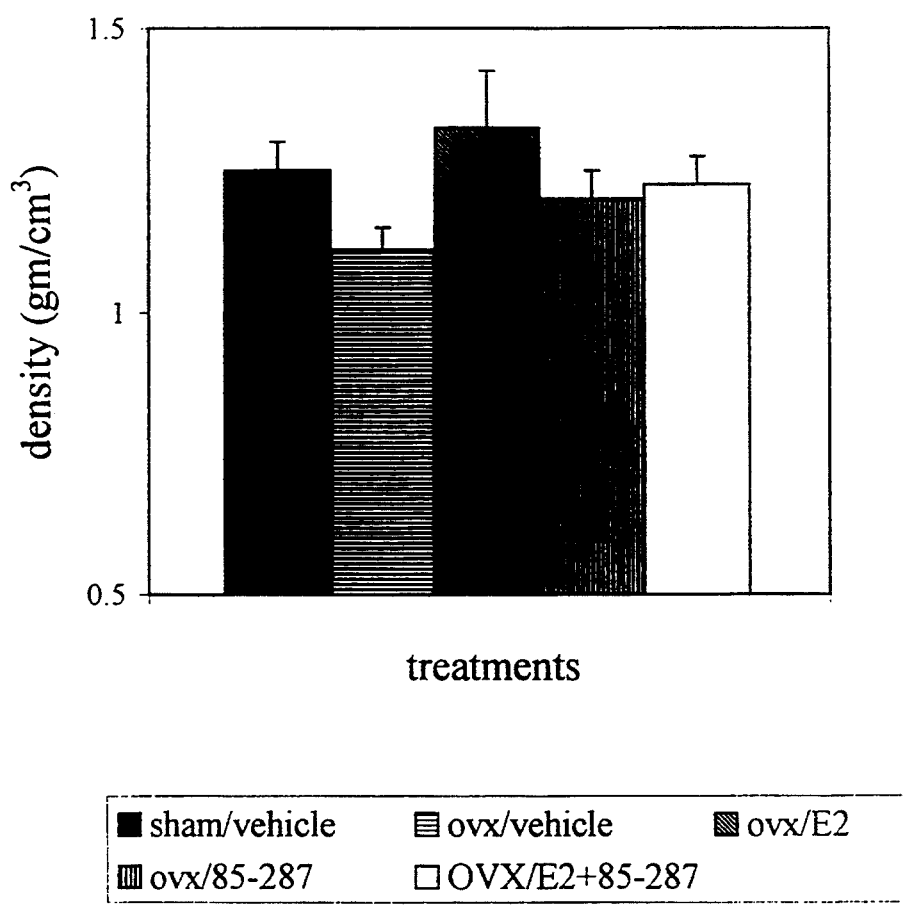
FIG. 2 illustrates the results of a study of the effects of a 2,3-diaryl-1-benzopyran on bone density in ovariectomized rats.

Data were analyzed by ANOVA and Fisher's PLSD using StatView ®software (Abacus Concepts, Inc., Berkeley, Calif.). Results are presented in the Table and in FIG. 2. There were significant differences between ovariectomized (ovx), vehicle-treated animals and ovariectomized, CDRI 287-treated animals. Differences between sham/vehicle animals and ovariectomized, CDRI 85/287-treated animals were not significant.

TABLE

| Treatment | Mean Difference | Fisher's PLSD |
|---|---|---|
| sham/vehicle vs. ovx/vehicle | 0.126 | 0.058* |
| sham/vehicle vs. ovx/CDRI 85/287 | 0.055 | 0.058 |
| sham/vehicle vs. ovx/E$_2$ | −0.078 | 0.058* |
| sham/vehicle vs. ovx/CDRI 85/287 + E$_2$ | 0.015 | 0.057 |
| ovx/vehicle vs. ovx/CDRI 85/287 | −0.071 | 0.057* |

*significant at 95%

Although the foregoing invention has been described in some detail by way of illustration and example for purposes of clarity of understanding, it will be evident that certain changes and modifications may be practiced within the scope of the appended claims.

What is claimed is:

1. A method for reducing bone loss in a patient comprising administering to a patient in need thereof an effective amount of a composition comprising a compound of the formula

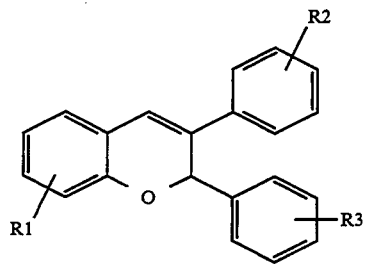

or a pharmaceutically acceptable salt thereof, wherein:
each of R1 and R2 is individually H, OH, linear or branched chain C$_1$–C$_{17}$ alkoxy, linear or branched chain C$_2$–C$_{18}$ acyloxy, or linear or branched chain C$_2$–C$_{18}$ alkoxycarbonyl; and
R3 is

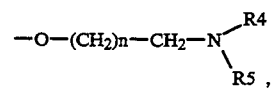

wherein each of R4 and R5 is individually a linear or branched chain alkyl radical of from one to 18 carbon atoms, or together with N, R4 and R5 form a three- to 10-membered ring, and n is an integer from 1 to 6,
in combination with a pharmaceutically acceptable carrier.

2. A method according to claim 1 wherein each of R1 and R2 is individually H, OH or C$_1$–C$_4$ alkoxy.

3. A method according to claim 1 wherein R1 is H or OH.

4. A method according to claim 1 wherein R2 is H or OH.

5. A method according to claim 1 wherein each of R4 and R5 is individually methyl, ethyl, propyl, isopropyl, butyl, isobutyl, sec-butyl or tert-butyl; or together with N, R4 and R5 form a five- or six-membered ring.

6. A method according to claim 1 wherein R3 is

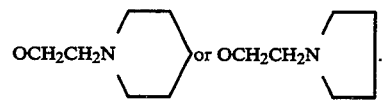

7. A method according to claim 6 wherein each of R1 and R2 is individually H or OH.

8. A method according to claim 1 wherein said compound is

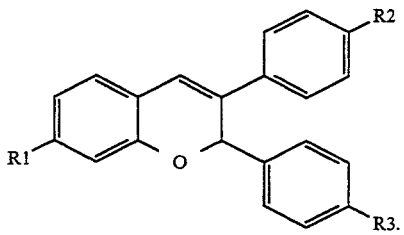

9. A method according to claim 8 wherein each of R1 and R2 is individually H or OH, and R3 is

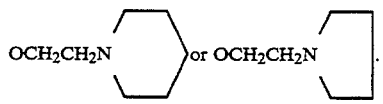

10. A method according to claim 1 wherein said bone loss is due to osteoporosis, Paget's disease, hypercalcemia of malignancy or hyperparathyroidism.

11. A method according to claim 1 wherein said patient is a post-menopausal female.

12. A method according to claim 1 wherein said composition is in a form suitable for oral administration.

13. A method according to claim 1 wherein said compound is administered at a dose of 0.1–5.0 mg/kg patient weight/day.

14. A method according to claim 1 wherein said composition is administered at daily to weekly intervals.

15. A method according to claim 1 wherein said composition is in the form of a subdermal implant.

16. A method for treating osteoporosis comprising administering to a patient a compound of the formula

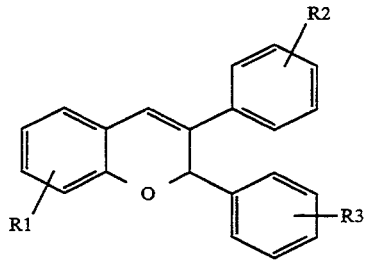

or a pharmaceutically acceptable salt thereof, wherein; each of R1 and R2 is individually H, OH, linear or branched chain $C_1$–$C_{17}$ alkoxy, linear or branched chain $C_2$–$C_{18}$ acyloxy, or linear or branched chain $C_2$–$C_{18}$ alkoxycarbonyl; and R3 is

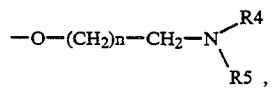

wherein each of R4 and R5 is individually a linear or branched chain alkyl radical of from one to 18 carbon atoms, or together with N, R4 and R5 form a three- to 10-membered ring, and n is an integer from 1 to 6, in combination with a pharmaceutically acceptable carrier in an amount sufficient to inhibit bone resorption.

17. A method according to claim 16 wherein each of R4 and R5 is individually methyl, ethyl, propyl, isopropyl, butyl, isobutyl, sec-butyl or tert-butyl; or together with N, R4 and R5 form a five- or six-membered ring.

18. A method according to claim 16 wherein R3 is

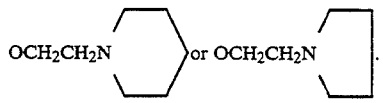

19. A method according to claim 16 wherein said compound is

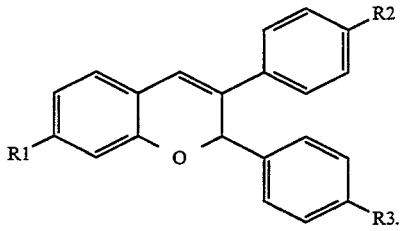

20. A method according to claim 19 wherein each of R1 and R2 is individually H or OH, and R3 is

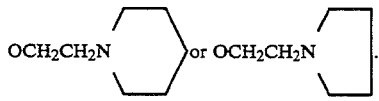

21. A method according to claim 16 wherein said patient is a post-menopausal female.

* * * * *